(12) United States Patent
Hyre

(10) Patent No.: US 9,569,649 B1
(45) Date of Patent: *Feb. 14, 2017

(54) EMBEDDED FAILURE DETECTION IN COMPOSITE MATERIAL

(71) Applicant: International Business Machines Corporation, Armonk, NY (US)

(72) Inventor: Bruce H. Hyre, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/162,344

(22) Filed: May 23, 2016

Related U.S. Application Data

(63) Continuation of application No. 14/984,691, filed on Dec. 30, 2015, now Pat. No. 9,389,072.

(51) Int. Cl.
G06K 7/10 (2006.01)
G01N 33/38 (2006.01)
G01N 27/20 (2006.01)

(52) U.S. Cl.
CPC ........... G06K 7/10366 (2013.01); G01N 27/20 (2013.01); G01N 33/383 (2013.01)

(58) Field of Classification Search
CPC ...... G01N 17/04; G01N 17/006; G01N 27/20; G01N 27/24; G01N 33/383; A61F 2002/30052; A61F 2002/30581; A61F 2002/3067; A61F 2002/30677; A61F 2002/488; A61F 2/24; A61F 2/30; A61F 2/30721; A61F 2/03

(Continued)

(56) References Cited

U.S. PATENT DOCUMENTS

| 5,321,358 A | * | 6/1994 | Mohr | G01R 33/44 324/300 |
| 8,423,300 B1 | * | 4/2013 | diGirolamo | G01B 21/32 324/700 |

(Continued)

OTHER PUBLICATIONS

List of IBM Patents or Patent Applications Treated as Related Form.

(Continued)

*Primary Examiner* — Fekadelelassie Girma
(74) *Attorney, Agent, or Firm* — Sherman IP LLP; Kenneth L. Sherman; Steven Laut

(57) ABSTRACT

A method for embedded failure detection includes embedding radio frequency identification (RFID) tags at varying depths within a composite material including a polymer, an epoxy or an aggregate bonded with a fluid. Each RFID tag is attached with an insulated wire loop and a sensor and configured to communicate tag identification and resistance on each insulated wire loop upon being energized by an RFID reader. The sensor may be for temperature, moisture, humidity, pressure, light, or acceleration. The RFID tags are read with an RFID reader after initial curing of the composite material for reference information. The RFID reader reads the RFID tags after a particular time period for current information. The current information is compared to the reference information. It is determined whether a change information has occurred for any of the RFID tags to detect a possible failure of the composite material.

1 Claim, 4 Drawing Sheets

(58) Field of Classification Search
USPC .......................................... 340/10.1, 853.2
See application file for complete search history.

(56) References Cited

U.S. PATENT DOCUMENTS

| | | | | |
|---|---|---|---|---|
| 8,886,468 B1* | 11/2014 | diGirolamo | ............ | G01B 21/32 |
| | | | | 324/700 |
| 2007/0260174 A1* | 11/2007 | Jung | ........................ | A61B 5/00 |
| | | | | 604/65 |
| 2009/0126471 A1* | 5/2009 | Fay | ..................... | G01M 5/0083 |
| | | | | 73/104 |
| 2009/0128169 A1* | 5/2009 | Fay | ........................ | G01N 17/04 |
| | | | | 324/700 |
| 2010/0052704 A1* | 3/2010 | Fay | ........................ | G01N 17/04 |
| | | | | 324/700 |
| 2010/0181477 A1* | 7/2010 | Okoli | ..................... | G01M 11/08 |
| | | | | 250/307 |
| 2010/0237994 A1* | 9/2010 | Carraher | ................. | H04L 41/12 |
| | | | | 340/10.1 |
| 2013/0281793 A1* | 10/2013 | Chen | ................. | A61M 5/14276 |
| | | | | 600/300 |
| 2014/0354443 A1* | 12/2014 | Roberson | .............. | E21B 47/122 |
| | | | | 340/853.2 |

OTHER PUBLICATIONS

International Business Machines Corporation, "Use RFID for material coherency control", Feb. 28, 2005, pp. 1-3, IPCOM000082458D, ip.com, United States.

Lesthaeghe, T. et al., "RFID Tags for Detecting Concrete Degradation in Bridge Decks", Institute for Transportation, Iowa State University, Dec. 2013, pp. 1-26, United States.

Mell, P., et al., "The NIST Definition of Cloud Computing", National Institute of Standards and Technology Special Publication 800-145, Sep. 2011, pp. 1-7, U.S. Department of Commerce, United States.

* cited by examiner

EMBEDDED FAILURE DETECTION IN COMPOSITE MATERIAL

BACKGROUND

Most of critical city (and corporate) infrastructure relies on concrete, cement, etc., yet this infrastructure is aging and fragile, and thus a potential threat to both economy and life. Any structure using concrete is subject to material failure, such as buildings, bridges, etc. This is an issue regardless of the cause: earthquake, fire, overload, impact, chemical attack (intentional or unintentional), etc., or simply just due to age. Given the opaque nature of concrete, evaluating the structural soundness of the concrete, or assessing for possible damage, is an expensive, complex, time-consuming effort, yet is required more and more due to the aging of critical infrastructure.

SUMMARY

Embodiments of the invention relate to embedded failure detection. One embodiment includes a method for embedded failure detection that includes embedding radio frequency identification (RFID) tags at varying depths within a composite material comprising a polymer, an epoxy or an aggregate bonded with a fluid. Each of the RFID tags are attached with an insulated wire loop and a sensor and configured to communicate tag identification and resistance on each insulated wire loop upon being energized by an RFID reader. The sensor comprises one of: a temperature sensor, a moisture sensor, a humidity sensor, a pressure sensor, a light sensor, or an accelerometer sensor. The method further includes reading, with the RFID reader, the RFID tags after initial curing of the composite material for reference information including a first resistance reading, a first position and a first location for each identified RFID tag of the plurality of RFID tags. The reference information is stored. The method further includes reading, by the RFID reader, the RFID tags after a particular time period for current information including a second resistance reading, a second position and a second location for each identified RFID tag. The current information is stored. The current information is compared to the reference information for each of the RFID tags. The method further includes determining whether a change in one or more of resistance, position and location has occurred for any of the RFID tags based on the comparing to detect a possible failure of the composite material.

These and other features, aspects and advantages of the present invention will become understood with reference to the following description, appended claims and accompanying figures.

DETAILED DESCRIPTION

Figure 1:
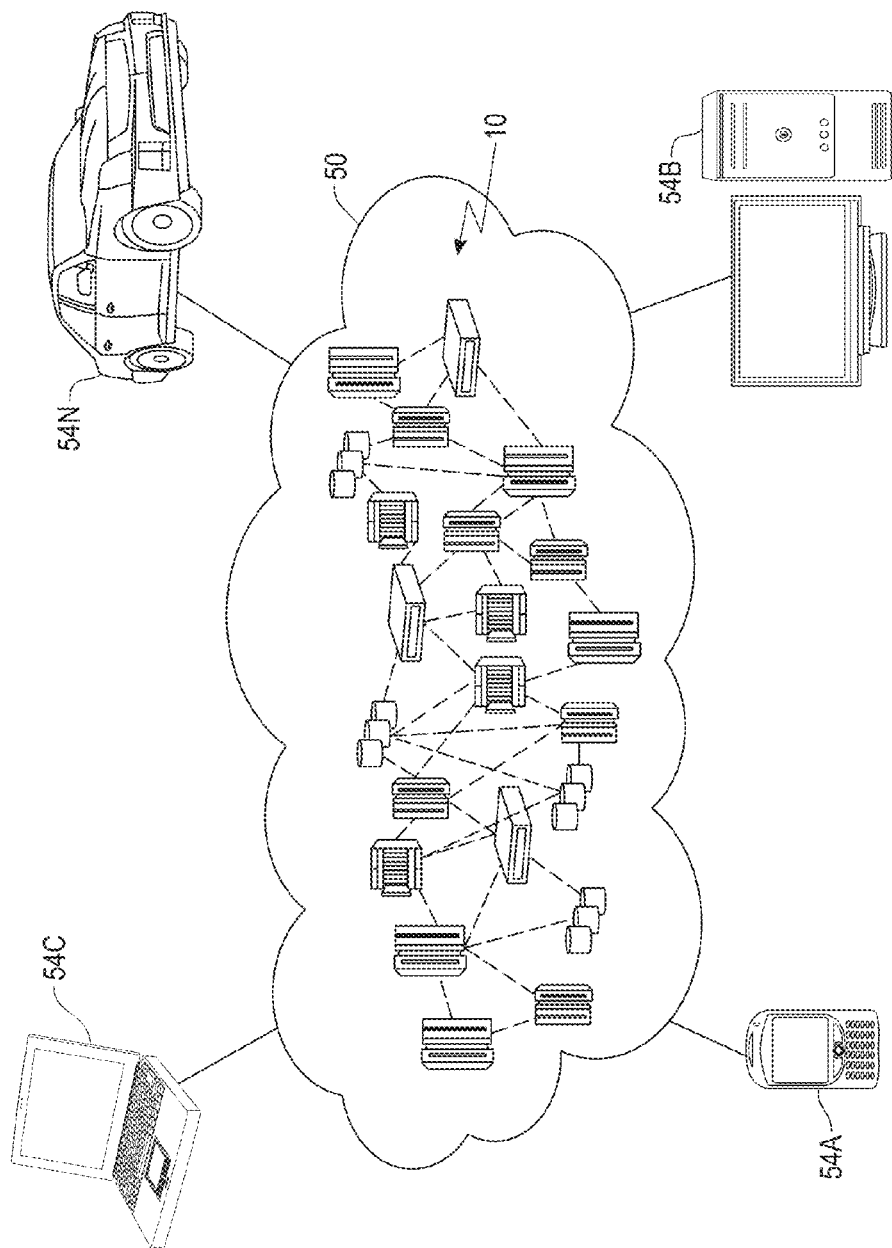
FIG. 1 depicts a cloud computing environment, according to an embodiment.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Current methods of internal inspection (such as X-ray, ultrasound, and Gamma scanners) require that expensive, complex devices be brought in, with highly trained operators, and must scan the composite material one position (image) at a time. This is both time consuming, and costly, resulting in infrequent, and often inadequate scanning, especially in hard-to-reach areas. The skill and attention to detail are critical to effective scanning—and often the weakest link in the chain (e.g., the most pervasive problems in the nuclear power plant industry are attributed to infrequent, poor, or incomplete material inspections during and after construction).

One or more embodiments provide passive RFID tags with one or more attached current loops. An RFID reader is implemented for reading the RFID tags. A calibration phase detects changes in composite material (e.g., concrete, cement, bricks, etc.) over time. Given the low cost of RFID tags, significant numbers may be distributed throughout the composite material, providing significantly better accuracy as compared to a physical inspection. If any cracks develop, these cracks will strain or break the wire loops, causing a change in the values when the tags are read again later.

It is understood in advance that although this disclosure includes a detailed description of cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines (VMs), and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed and automatically, without requiring human interaction with the service's provider.

Broad network access: capabilities are available over a network and accessed through standard mechanisms that promote use by heterogeneous, thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned and, in some cases, automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active consumer accounts). Resource usage can be monitored, controlled, and reported, thereby providing transparency for both the provider and consumer of the utilized service.

Service Models are as follows:

Software as a Service (SaaS): the capability provided to the consumer is the ability to use the provider's applications running on a cloud infrastructure. The applications are accessible from various client devices through a thin client interface, such as a web browser (e.g., web-based email). The consumer does not manage or control the underlying cloud infrastructure including network, servers, operating systems, storage, or even individual application capabilities, with the possible exception of limited consumer-specific application configuration settings.

Platform as a Service (PaaS): the capability provided to the consumer is the ability to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application-hosting environment configurations.

Infrastructure as a Service (IaaS): the capability provided to the consumer is the ability to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is a service oriented with a focus on statelessness, low coupling, modularity, and semantic interoperability. At the heart of cloud computing is an infrastructure comprising a network of interconnected nodes.

Referring now to FIG. 1, an illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as private, community, public, or hybrid clouds as described hereinabove, or a combination thereof. This allows the cloud computing environment 50 to offer infrastructure, platforms, and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 2:
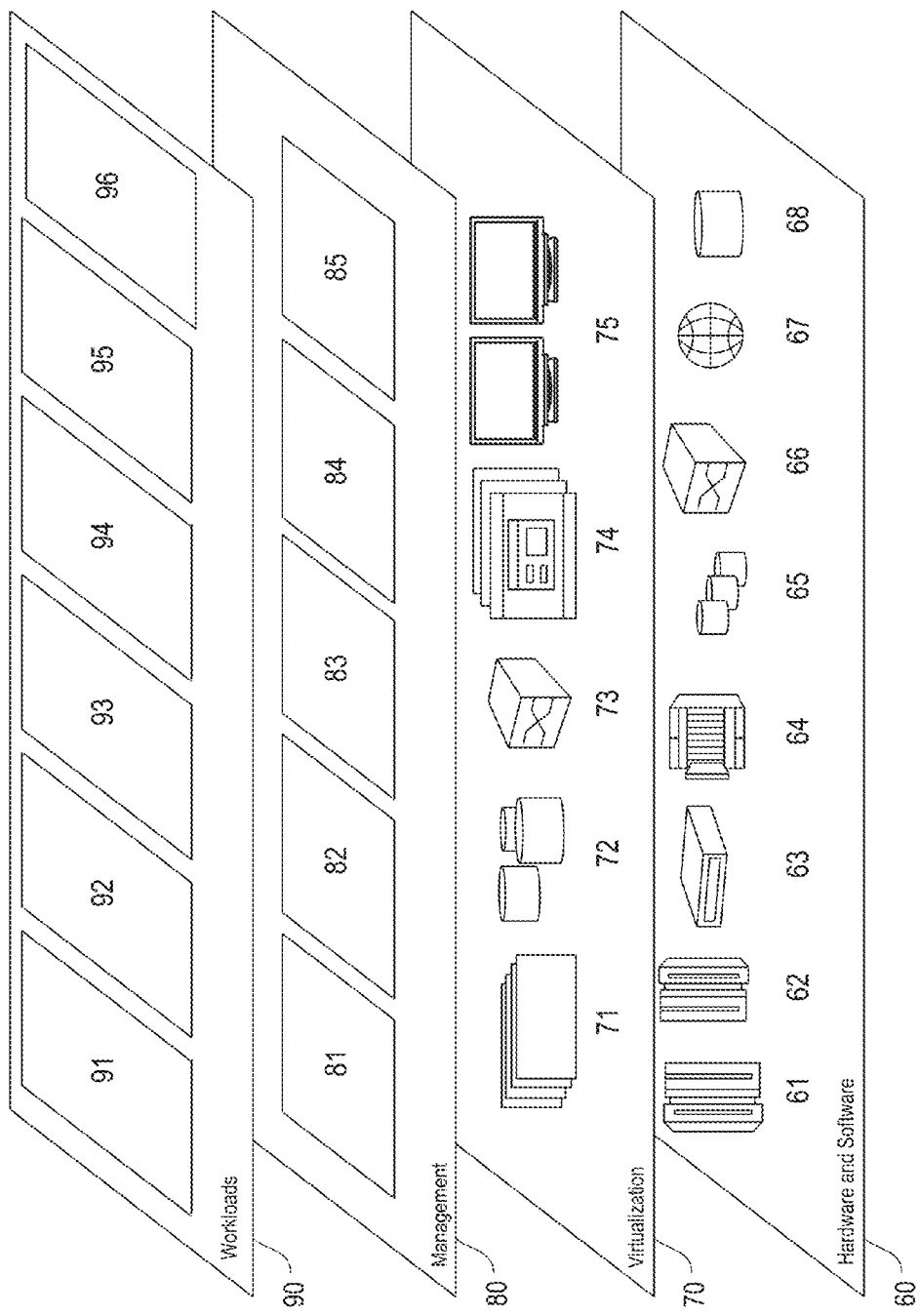
FIG. 2 depicts a set of abstraction model layers, according to an embodiment.

Referring now to FIG. 2, a set of functional abstraction layers provided by the cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, a management layer 80 may provide the functions described below. Resource provisioning 81 provides dynamic procurement of computing resources and other resources that are utilized to perform tasks within the cloud computing environment. Metering and pricing 82 provide cost tracking as resources are utilized within the cloud computing environment and billing or invoicing for consumption of these resources. In one example, these resources may comprise application software licenses. Security provides identity verification for cloud consumers and tasks as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95 and embedded failure detection 96. As mentioned above, all of the foregoing examples described with respect to FIG. 2 are illustrative only, and the invention is not limited to these examples.

It is understood all functions of one or more embodiments as described herein may be typically performed in the computing environment 50 (FIG. 1), or the environment 300 (FIG. 3), which can be tangibly embodied as hardware processors and with modules of program code. However, this need not be the case. Rather, the functionality recited herein could be carried out/implemented and/or enabled by any of the layers 60, 70, 80 and 90 shown in FIG. 2.

It is reiterated that although this disclosure includes a detailed description on cloud computing, implementation of the teachings recited herein are not limited to a cloud computing environment. Rather, the embodiments of the present invention may be implemented with any type of clustered computing environment now known or later developed.

Figure 3:
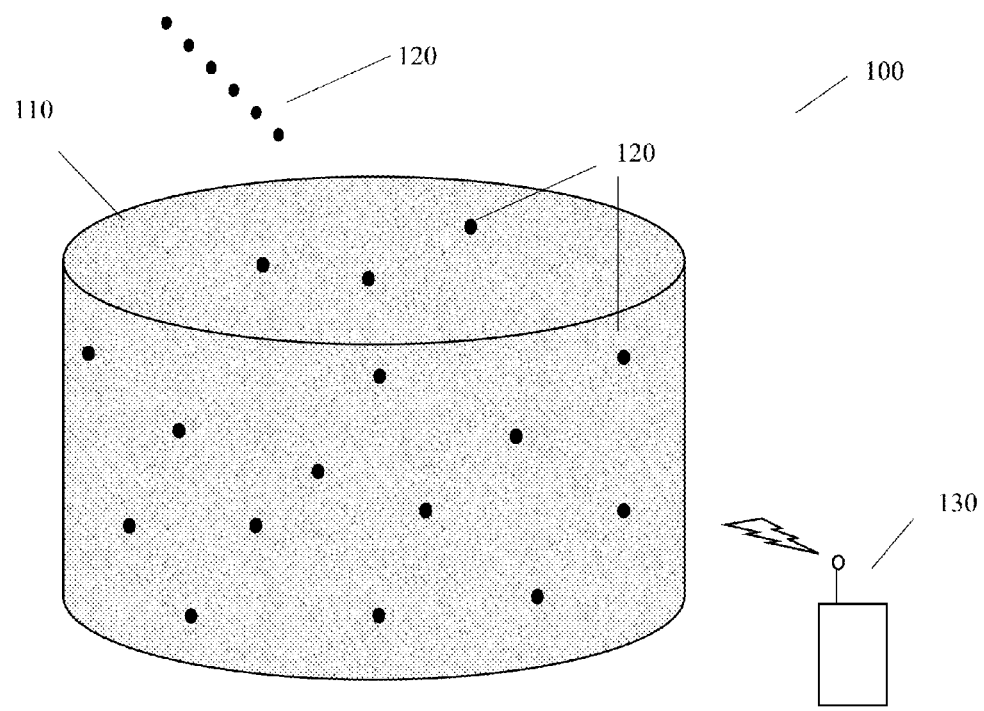
FIG. 3 is an example embedding of RFID tags attached with one or more insulated wire loops in composite material, according to an embodiment of the present invention.
Figure 4:
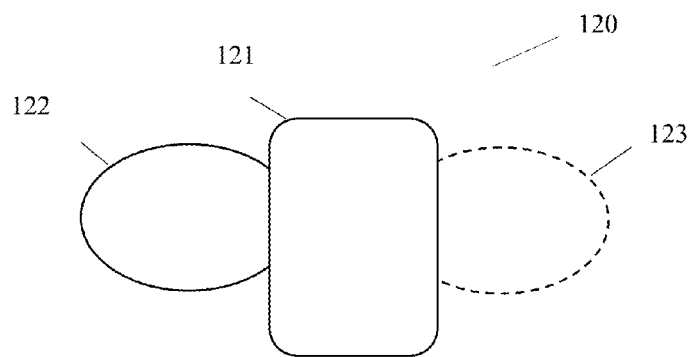
FIG. 4 shows an RFID tag connected with one or more insulated wire loops, according to an embodiment.

FIG. 3 is an example 100 of embedding of RFID tags 120 attached with one or more insulated wire loops 122 or 123 (FIG. 4) in composite material 110, according to an embodiment of the present invention. The composite material 110 may be any material that includes a polymer, an epoxy, an aggregate bonded with fluid, such as concrete, bricks, etc. As shown in FIG. 4, an insulated wire loop 122 is attached to an RFID circuit 121 as a "current loop" (e.g., a simple loop of insulated, conductive wire) for the RFID tag 120. In one embodiment, additional wire loops 123 may be added to the RFID circuits 121 that may have the same or varied lengths.

Returning to FIG. 3, in one embodiment the RFID tags 120 report back the resistance on each loop 122/123 when energized (scanned) with an active RFID reader 130 (in addition to the usual RFID type information, such as a unique identifier, etc.). In one example, the RFID tags 120 are embedded in the wet composite material 110, just before (or during) the pouring of the composite material. Any number of RFID tags 120 may be mixed at any depth, as desired or required by the application.

In one embodiment, as some RFID tags 120 may become damaged in the embedding/mixing/pouring process, once the material has completed curing ("set"), a calibration cycle is conducted. In one example, the RFID tags 120 are all read using the active RFID reader 130, and the results are recorded along with the position where the tags are located. In one example, the recorded information may be stored on the active RFID reader 130, or stored in the cloud environment 50 (FIG. 1). The initial reading forms the baseline, or reference read, and indicates which RFID tags 120 are known as being active or inactive (e.g., damaged) at construction time.

In one embodiment, later inspections are quick, inexpensive, and easy to conduct. In one example, the active RFID reader 130 may be a standard, low-cost RFID reader that is passed over the composite material 110, energizing the RFID tags 120, causing them to "read" the current loops (wire loop 122 (and optional additional wire loops 123) attached to them, and report back the results. The results are recorded, and compared to the original baseline either on the active RFID reader 130 or computed in the cloud environment 50 (FIG. 1). If, for example, a crack in the composite material 110 forms across any of the wire loops 122/123 (current loops), the wire loop 122/123 will become broken, or the resistance changed. When the RFID tag 120 that the wire loop 122/123 is attached to is energized, it will try to pass current through the loop, and either get infinite resistance (broken wire loop="big" crack or displacement), or increased resistance (from stretching/thinning of the wire="small" crack or displacement). If any changes are detected in these values versus the baseline, then more sophisticated (and expensive) equipment may be brought in as needed to conduct further testing of the composite material 110. However, these sophisticated scans will now be much faster, cheaper, and better, as there is no need to inspect the entire structure as the active RFID reader 130 can determine position/location of the area in question based on knowing the position/location of the damaged RFID tag 120. Therefore, a more thorough deep inspection can be performed on the known bad area(s).

In one embodiment, the deployment of the RIFD tags 120 and testing of the wire loops 122/123 may be used with any poured, or cast, building material, and implemented in block material (brick, concrete). In another embodiment, the reference scan may be correlated with a traditional inspection (X-ray, Gamma, etc.), to ensure the material is sound to begin with, and as a better reference baseline.

In one embodiment, additional sensors may easily be added to the RFID tags 120, such as temperature, moisture, humidity, pressure, light, accelerometers, etc. In another embodiment, continuous scans may be performed from the beginning, or implemented at a later date, by installing one or more permanent active RFID readers 130 that continually scan the RFID tags 120 nearby. Given that tags can be read at upwards of 400 tags a second, a very thorough, complete scan could be performed every few seconds.

Figure 5:
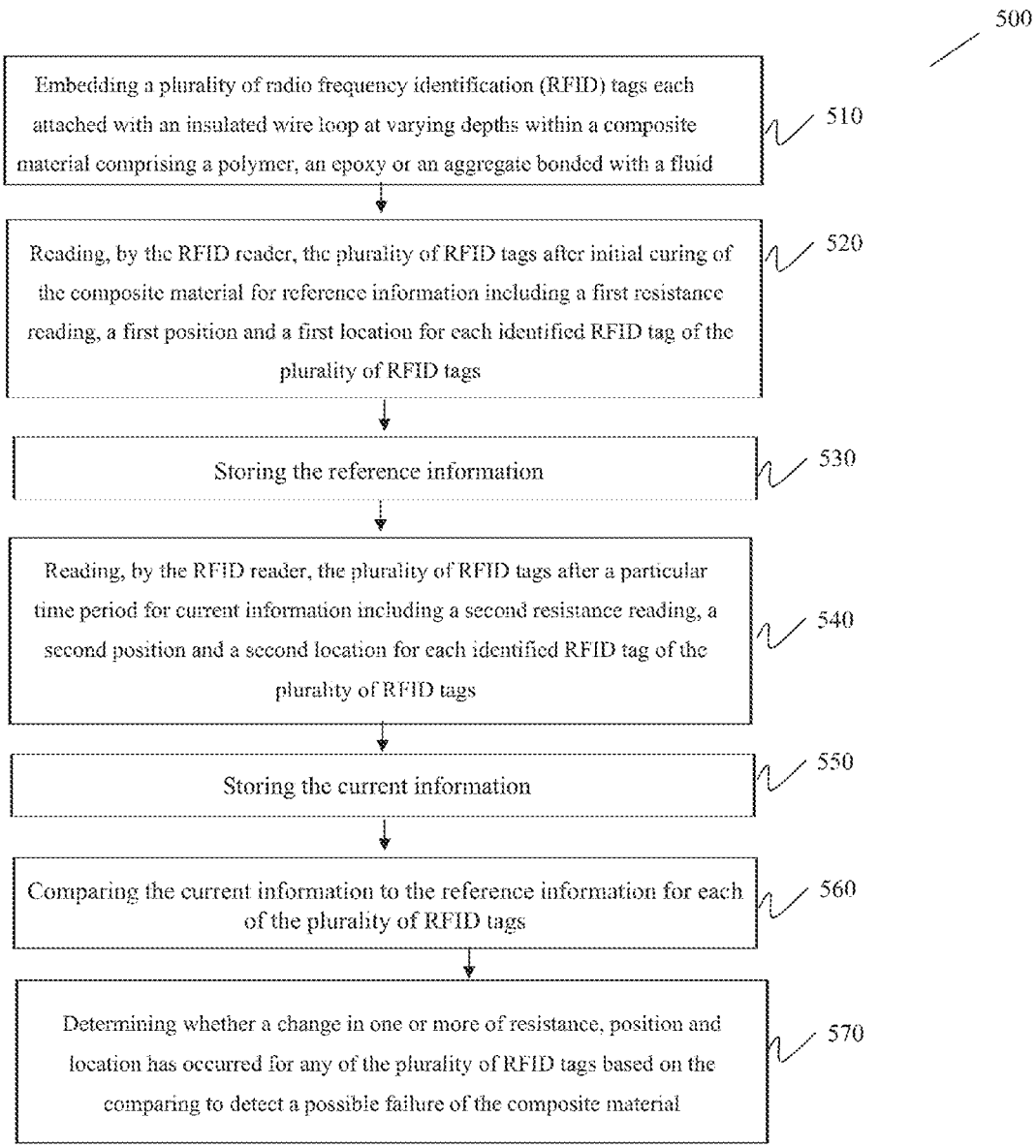
FIG. 5 illustrates a block diagram for a process for embedded failure detection, according to one embodiment.

FIG. 5 illustrates a block diagram for a process 500 for embedded failure detection, according to one embodiment. In block 510 multiple RFID tags (e.g., RFID tags 120, FIGS. 3-4) are embedded at varying depths within a composite material (e.g., composite material 110 (FIG. 3). The RFID tags are each attached with an insulated wire loop, and the composite material comprises aggregate bonded with a fluid (e.g., concrete, etc.). Each of the multiple RFID tags are configured to communicate tag identification and resistance on each insulated wire loop upon being energized by an RFID reader (e.g., RFID reader 130). Additionally, other information is reported from the RFID tags as well (e.g., location or position information). In block 520, process 500 includes reading, by the RFID reader, the RFID tags after initial curing of the composite material for reference information including a first resistance reading, a first position and a first location for each identified RFID tag of the multiple RFID tags. In block 530, the reference information is stored (e.g., on the RFID reader or in a cloud environment 50, FIG. 1). In block 540, process 500 provides for reading, by the RFID reader, the multiple RFID tags after a particular time period (e.g., a month, a year, etc.) for current information including a second resistance reading, a second position and a second location for each identified RFID tag of the multiple RFID tags. In block 550 the current information is stored (e.g., on the RFID reader or in the cloud environment 50). In block 560 the current information is compared to the reference information for each of the multiple RFID tags. In block 570 process 500 includes determining whether a change in one or more of resistance, position and location has occurred for any of the multiple RFID tags based on the comparison to detect a possible failure of the composite material.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for embedded failure detection comprising:
    embedding a plurality of radio frequency identification (RFID) tags at varying depths within a composite material, the RFID tags are each attached with an insulated wire loop and a sensor, the composite material comprises a polymer, an epoxy or an aggregate bonded with a fluid, wherein each of the plurality of RFID tags are configured to communicate tag identification and resistance on each insulated wire loop upon being energized by an RFID reader, and the sensor comprises one of: a temperature sensor, a moisture sensor, a humidity sensor, a pressure sensor, a light sensor, or an accelerometer sensor;
    reading, by the RFID reader, the plurality of RFID tags after initial curing of the composite material for reference information including a first resistance reading, a first position and a first location for each identified RFID tag of the plurality of RFID tags;
    storing the reference information;
    reading, by the RFID reader, the plurality of RFID tags after a particular time period for current information including a second resistance reading, a second position and a second location for each identified RFID tag of the plurality of RFID tags;
    storing the current information;
    comparing the current information to the reference information for each of the plurality of RFID tags; and
    determining whether a change in one or more of resistance, position and location has occurred for any of the plurality of RFID tags based on the comparing to detect a possible failure of the composite material.

* * * * *